(12) United States Patent
Hagemeyer et al.

(10) Patent No.: US 9,365,433 B2
(45) Date of Patent: Jun. 14, 2016

(54) METHOD FOR THE PRODUCTION OF A NANOCRYSTALLINE MOLYBDENUM MIXED OXIDE

(75) Inventors: Alfred Hagemeyer, Bad Aibling (DE); Gerhard Mestl, München (DE); Silvia Neumann, Grosskarolinenfeld (DE); Hans-Jörg Wölk, Rosenheim (DE)

(73) Assignee: SUED-CHEMIE IP GMBH & CO. KG, Munich (DE)

( * ) Notice: Subject to any disclaimer, the term of this patent is extended or adjusted under 35 U.S.C. 154(b) by 405 days.

(21) Appl. No.: 12/935,707

(22) PCT Filed: Apr. 3, 2009

(86) PCT No.: PCT/EP2009/002476
§ 371 (c)(1),
(2), (4) Date: Dec. 13, 2010

(87) PCT Pub. No.: WO2009/121626
PCT Pub. Date: Oct. 8, 2009

(65) Prior Publication Data
US 2011/0105790 A1    May 5, 2011

(30) Foreign Application Priority Data
Apr. 4, 2008 (DE) .......................... 10 2008 017 311

(51) Int. Cl.
| | |
|---|---|
| *C01G 3/00* | (2006.01) |
| *C01G 39/00* | (2006.01) |
| *C01G 49/00* | (2006.01) |
| *C01G 31/00* | (2006.01) |
| *B01J 23/00* | (2006.01) |
| *B01J 23/28* | (2006.01) |
| *B01J 23/887* | (2006.01) |
| *B01J 23/888* | (2006.01) |
| *B01J 35/00* | (2006.01) |
| *B01J 37/00* | (2006.01) |
| *B01J 37/02* | (2006.01) |
| *B01J 37/08* | (2006.01) |
| *C01G 41/00* | (2006.01) |
| *C07C 51/235* | (2006.01) |
| *B01J 35/10* | (2006.01) |

(52) U.S. Cl.
CPC .............. *C01G 39/00* (2013.01); *B01J 23/002* (2013.01); *B01J 23/28* (2013.01); *B01J 23/887* (2013.01); *B01J 23/8885* (2013.01); *B01J 35/0013* (2013.01); *B01J 37/0045* (2013.01); *B01J 37/0236* (2013.01); *B01J 37/08* (2013.01); *C01G 3/006* (2013.01); *C01G 31/006* (2013.01); *C01G 39/006* (2013.01); *C01G 41/006* (2013.01); *C01G 49/009* (2013.01); *C07C 51/235* (2013.01); *B01J 35/002* (2013.01); *B01J 35/1009* (2013.01); *B01J 2523/00* (2013.01); *C01P 2002/72* (2013.01); *C01P 2006/12* (2013.01)

(58) Field of Classification Search
None
See application file for complete search history.

(56) References Cited

U.S. PATENT DOCUMENTS

| | | |
|---|---|---|
| 5,583,084 A | 12/1996 | Martin et al. |
| 5,885,922 A | 3/1999 | Hibst et al. |
| 6,124,499 A | 9/2000 | Hibst et al. |
| 7,345,198 B2 | 3/2008 | Dubois et al. |
| 7,390,766 B1 | 6/2008 | Klein |
| 2006/0128989 A1* | 6/2006 | Dubois et al. ............... 562/547 |
| 2006/0183941 A1 | 8/2006 | Dubois et al. |
| 2008/0161602 A1 | 7/2008 | Wang et al. |
| 2009/0105507 A1* | 4/2009 | Dubois et al. ............... 568/594 |
| 2009/0325794 A1* | 12/2009 | Wolk et al. ................... 502/324 |
| 2010/0015446 A1 | 1/2010 | Wölk |

FOREIGN PATENT DOCUMENTS

| | | |
|---|---|---|
| DE | 101 09 892 A1 | 9/2002 |
| DE | 10 206 032 452 A1 | 1/2008 |
| FR | 2 826 959 | 1/2003 |
| GB | 1 538 107 | 1/1979 |
| JP | 2005-538173 | 12/2005 |
| WO | WO 2004/024666 A1 | 3/2004 |
| WO | WO 2005/051539 A1 | 6/2005 |
| WO | WO 2008/006565 A1 | 1/2008 |
| WO | WO 2008/028681 A2 | 3/2008 |

OTHER PUBLICATIONS

G. A. Zenkovets et al., "The structural genesis of a complex MoVW)$_x$O$_{14}$ oxide during thermal treatments and its redox behavior at elevated temperatures," Materials Chemistry and Physics, 103 (2007), 295-304.

O. Ovsitser et al., "Molybdenum oxide based partial oxidation catalyst Part 3. Structural changes of a MoVW mixed oxide catalyst during activation and relation to catalytic performance in acrolein oxidation," Journal of Molecular Catalysis A:Chemical 195 (2002), 291-303.

International Search Report of PCT/EP2009/002476, dated Jul. 23, 2009.

* cited by examiner

Primary Examiner — Steven Bos
(74) Attorney, Agent, or Firm — Anthony A. Biscula

(57) ABSTRACT

A method for the production of a nanocrystalline molybdenum mixed oxide, the use of the molybdenum mixed oxide as catalyst for chemical conversions, in particular for a conversion of acrolein to acrylic acid as well as a catalyst that contains the molybdenum mixed oxide.

4 Claims, 2 Drawing Sheets

METHOD FOR THE PRODUCTION OF A NANOCRYSTALLINE MOLYBDENUM MIXED OXIDE

CROSS REFERENCE TO RELATED APPLICATIONS

This is a National Phase application of PCT application number PCT/EP2009/002476, filed Apr. 3, 2009, which claims priority benefit of German application number DE 10 2008 017 311.8, filed Apr. 4, 2008, the content of such applications being incorporated herein by reference.

FIELD OF THE INVENTION

The invention relates to a method for the production of a nanocrystalline molybdenum mixed oxide, the use of the molybdenum mixed oxide as catalyst for chemical conversions as well as a catalyst which contains the molybdenum mixed oxide.

BACKGROUND OF THE INVENTION

Until now, molybdenum mixed oxides have been obtained in the state of the art by precipitation methods, sol-gel methods or solid-state reactions.

Molybdenum mixed oxides are used in the state of the art as catalyst for chemical conversions. Conversions of alkyl compounds or alkene compounds to acrolein or derivatives thereof as well as a conversion of acrolein to acrylic acid may be named here as examples. The molybdenum mixed oxide catalysts according to the state of the art often do not display a sufficient activity in these reactions.

WO 2008/028681 and WO 2008/006565 A1 disclose a method for the production of nanocrystalline metal oxides or mixed metal oxides. There is no indication in these documents that special nanocrystalline molybdenum mixed oxides which are particularly well-suited as catalyst in particular for the conversion of acrolein to acrylic acid can be produced with the method.

A crystalline molybdenum mixed oxide can be obtained only with difficulty via conventional methods. Thus, G. A. Zenkovets et al., "The structural genesis of a complex $(MoVW)_5O_{14}$ oxide during thermal treatments and its redox behaviour at elevated temperatures", Materials Chemistry and Physics, 103 (2007), 295-304, disclose that an $Mo_{0.68}V_{0.23}W_{0.09}O_x$ mixed oxide obtained via spray drying has an amorphous structure. This mixed oxide is present in the form of large aggregates approximately 5 μm in size. A partially nanocrystalline structure forms inside the aggregates due to subsequent calcining. A pure crystalline phase with crystallites more than 1000 nm in size forms only after prolonged thermal treatment at approximately 440° C. The production of a nanocrystalline molybdenum mixed oxide can thus be accomplished only with difficulty.

It is clear from O. Ovsiter et al., "Molybdenum oxide based partial oxidation catalyst Part 3", Journal of Molecular Catalysis A: Chemical 185 (2002), 291-303, that a molybdenum mixed oxide does not display well-crystallized particles after thermal treatment. A crystalline phase, however, was able to be observed during a conversion of acrolein to acrylic acid, i.e. a crystallization first takes place during the oxidation reaction. Such a catalyst thus has a sufficient activity only after a prolonged reaction period.

A disadvantage of the molybdenum mixed oxides described in the state of the art is thus that a uniform particle size of the molybdenum mixed oxides cannot be obtained and a control of the crystallization, in particular with regard to the crystallite size, is not possible. The BET surface area of the molybdenum mixed oxides described in the state of the art is likewise mostly too small. A small particle size with as large as possible a BET surface area is desired, in particular for catalytic uses.

DESCRIPTION OF THE INVENTION

An object of the present invention was thus the provision of a nanocrystalline molybdenum mixed oxide which, in catalytic conversions, in particular in a conversion of acrolein to acrylic acid, has an increased activity and selectivity.

This object is achieved by a method for the production of a nanocrystalline molybdenum mixed oxide, comprising the steps of
a) the introduction of a solution, suspension or slurry which contains a molybdenum starting compound and at least one further metal-containing starting compound, selected from a tungsten-containing and/or vanadium-containing starting compound, into a reaction chamber by means of a carrier fluid,
b) a thermal treatment of the solution, suspension or slurry which contains the molybdenum starting compound and the at least one further metal-containing starting compound in a treatment zone by means of a pulsating flow at a temperature of from 200 to 500° C.,
c) the formation of nanocrystalline molybdenum mixed oxide,
d) the discharge of the nanocrystalline molybdenum mixed oxide obtained in steps b) and c) from the reactor.

It was surprisingly found that a uniform particle size of the molybdenum mixed oxides can be obtained by the method according to aspects of the invention and a control of the crystallization, in particular with regard to the crystallite size, is achieved. The BET surface area was likewise able to be increased compared with the molybdenum mixed oxides known in the state of the art.

The molybdenum mixed oxide obtained according to aspects of the invention is characterized by a crystallite size in the range of from 5 nm to 450 nm.

The catalytic activity of a catalyst containing the molybdenum mixed oxide obtained according to aspects of the invention, in particular in the case of a conversion of acrolein to acrylic acid, was able to be increased by roughly 1% compared with known conventional catalysts.

By the term "mixed oxide" is meant within the meaning of the invention a mixed oxide that comprises two or more metals and constitutes a single chemical compound that can be expressed with a formula. This is to be distinguished accordingly from a pure (physical) mixture of several metal oxides.

Preferably a molybdate, particularly preferably ammonium heptamolybdate tetrahydrate, is used as molybdenum starting compound. However, it is clear to a person skilled in the art in this field that other molybdates and molybdenum compounds known in the state of the art can also be used.

In order to obtain a mixed oxide, at least one further metal-containing starting compound should be used. Tungstates and/or vanadates are preferred further compounds according to aspects of the present invention. The further starting compound ammonium metatungstate and/or ammonium metavanadate is particularly preferred. A combination of the two last named is most preferred.

The molybdenum starting compound and the at least one further metal-containing starting compounds are preferably used together as solution, suspension or slurry. It is most preferred if the starting compounds are present in solution, in particular in aqueous solution. If necessary, the solution can be heated in order to achieve a complete dissolution of the starting compounds, in particular in the case of poorly soluble starting compounds. The solution of the starting compounds is advantageously heated to >50° C.

In a particularly preferred embodiment, a solution of ammonium metatungstate, ammonium heptamolybdate tetrahydrate and ammonium metavanadate is used in the method according to aspects of the invention.

Prior to or during the introduction into the reaction chamber, a solution, suspension or slurry which contains at least one additional metal salt can be added to the solution, suspension or slurry which contains the molybdenum starting compound and the at least one further metal-containing starting compound. The at least one metal salt is preferably a copper salt or an iron salt or a combination of a copper and an iron salt.

The addition of a solution, suspension or slurry containing metal salt to the solution, suspension or slurry which contains the molybdenum starting compound and the at least one further metal-containing starting compound brings about a doping of the resulting molybdenum mixed oxide with the corresponding metal. Any fine adjustments for the respective desired catalytic function of the molybdenum mixed oxide can thereby be achieved.

In a particularly preferred embodiment, a solution of ammonium metatungstate, ammonium heptamolybdate tetrahydrate and ammonium metavanadate, to which a copper-salt solution is added, is used in the method according to aspects of the invention. The copper salt is preferably copper sulphate or copper acetate.

In a further particularly preferred embodiment, a solution of ammonium metatungstate, ammonium heptamolybdate tetrahydrate and ammonium metavanadate, to which a copper-salt and iron-salt solution is added, is used in the method according to aspects of the invention. The copper salt is preferably copper sulphate or copper acetate and the iron salt is preferably iron nitrate.

It was surprisingly found that the method can be carried out at relatively low temperatures of from 200 to 500° C., particularly preferably from 250 to 450° C., particularly preferably from 300 to 400° C. Hitherto, preferred temperatures of more than 700° C., indeed up to 1400° C., were known in the state of the art. Quite particularly surprisingly, it was also found that the crystallization process of the molybdenum mixed oxide can be controlled in a targeted manner by the method according to aspects of the invention, in particular the size of the crystallites and the pore-size distribution of the corresponding molybdenum mixed oxides. This can further be advantageously influenced by the residence time in the flame or by the reactor temperature. The nanocrystalline molybdenum mixed oxide particles that form are prevented from agglomerating by the pulsating thermal treatment. Typically, the nanocrystalline particles are immediately transferred by the stream of hot gas into a colder zone, where some of the molybdenum mixed oxide crystallites are obtained with diameters of even less than 20 nm.

In the case of the thus-obtainable molybdenum mixed oxide crystallites, this leads to clearly increased BET surface areas of >1 $m^2/g$, particularly preferably 2 to 10 $m^2/g$ and particularly preferably 3 to 7 $m^2/g$. The BET surface area is determined using the Brunauer, Emmett and Teller method according to DIN 66132.

In the method according to aspects of the invention, suspensions can be calcined within a very short period, typically within a few milliseconds, at comparatively lower temperatures than are usual with methods of the state of the art, without additional filtration and/or drying steps or without the addition of additional solvents. The molybdenum mixed oxide nanocrystallites that form have significantly increased BET surface areas and thus represent a molybdenum mixed oxide catalyst with increased reactivity, improved rate of conversion and improved selectivity, in particular with regard to a conversion of acrolein to acrylic acid.

The nearly identical residence time of every molybdenum mixed oxide particle in the homogeneous temperature field created by the method results in an extremely homogeneous end product with narrow monomodal particle distribution. A device for carrying out the method according to aspects of the invention in the production of such monomodal nanocrystalline metal oxide powders is known for example from DE 101 09 892 A1. Unlike the device described there and the method disclosed there, the present method does not, however, require an upstream evaporation step in which the starting material, i.e. the molybdenum starting compound, is heated to an evaporation temperature.

The molybdenum starting compound and the further starting compounds from which the molybdenum mixed oxides according to aspects of the invention are produced are inserted directly via a carrier fluid, in particular a carrier gas, preferably an inert carrier gas, such as for example nitrogen, etc., into so-called reaction chambers, i.e. into the combustion chamber. Attached exhaust side to the reaction chamber is a resonance tube with a flow cross-section which is clearly reduced compared with the reaction chamber. The floor of the combustion chamber is equipped with several valves for the entry of the combustion air into the combustion chamber. The aerodynamic valves are fluidically and acoustically matched with the combustion chamber and the resonance tube geometry such that the pressure waves, created in the combustion chamber, of the homogeneous "flameless" temperature field spread pulsating predominantly in the resonance tube. A so-called Helmholtz resonator forms with pulsating flow with a pulsation frequency of between 10 and 150 Hz, preferably 30 to 110 Hz.

Material is typically fed into the reaction chamber either with an injector or with a suitable two-component nozzle or in a Schenk dispenser.

Preferably, the molybdenum starting compound is introduced into the reaction chamber in atomized form, with the result that a fine distribution in the region of the treatment zones is guaranteed.

After the thermal treatment, the nanocrystalline molybdenum mixed oxides that form are immediately transferred into a colder zone of the reaction chamber, if possible by means of the carrier fluid, with the result that they can be separated and discharged in the colder zone. The yield of the method according to aspects of the invention is almost 100%, as all of the product that forms can be discharged from the reactor.

Typically, the method is carried out at a pressure of between 15 and 40 bar.

A subject of the invention is furthermore the nanocrystalline molybdenum mixed oxide that can be obtained by the method according to aspects of the invention. It was found that the thus-obtainable nanocrystalline molybdenum oxide preferably has a crystallite size in the range of from 5 nm to 450 nm, preferably of from 10 nm to 400 nm, quite particularly preferably 15 to 250 nm, which, as already stated above, can preferably be set by the pulsation of the thermal treatment. The particle size can be determined by XRD or TEM.

Furthermore, molybdenum oxide particles which have a BET surface area of preferably >1 $m^2/g$, particularly preferably 2 to 10 $m^2/g$ and particularly preferably 3 to 7 $m^2/g$ are obtained by the method according to aspects of the invention.

The molybdenum mixed oxide obtained according to aspects of the invention is exceptionally suitable for use as catalyst, for example in the catalytic conversion of acrolein to acrylic acid.

Acrylic acid or propenoic acid belongs to the unsaturated carboxylic acids. Acrylic acid is a colourless chemical compound, with a pungent, vinegary odour, that can be mixed with water and is liquid at room temperature. Acrylic acid has a strong corrosive action and is flammable. Large-scale industrial production usually takes place by a two-stage oxidation of propylene with the aid of catalysts. In the first stage, propylene is converted with air to propenal (acrolein). The oxidation of propenal to acrylic acid takes place in the second stage. Its main use is polymerization to superabsorbent polymers (use e.g. in nappies), acrylate esters (which are in turn used for the production of polymers) and as comonomers in the production of polymer dispersions. The water-soluble polymerisates of acrylic acid are used as finishes and thickeners as well as coatings for solid dosage forms and as ointment bases. Polyacrylic acid ethyl ester has proved its worth as copolymerization partner for the production of weather-proof elastomers.

A subject of the invention is thus also a catalyst which contains the molybdenum mixed oxide according to aspects of the invention. The catalyst can be a supported or an unsupported catalyst (bulk catalyst, extruded catalyst).

In an embodiment of the present invention, the molybdenum mixed oxide can be processed together with a suitable binder to an extrudate (tablets, shaped bodies, honeycomb bodies and the like). Any binder that is familiar to a person skilled in the art and appears suitable, in particular silicate materials, aluminium oxide, zirconium compounds, titanium oxide, as well as their mixtures, and materials such as e.g. cement, clay, silica/alumina, can be used as binders. Preferred binders are, among others, pseudoboehmite as well as siliceous binders such as colloidal silicon oxide or silica sol.

In preferred developments of the invention, the molybdenum mixed oxide can furthermore be processed together with other components, preferably with a binder, particularly preferably with an organic binder, for example organic glues, polymers, resins or waxes, to a washcoat which can be applied to a metallic or ceramic support. Optionally, additional impregnating steps or calcining steps can take place. Preferably, the molybdenum mixed oxide obtained according to aspects of the invention is present as coating on a support. A preferred support material is steatite, steatite spheres are particularly preferred. The coating is preferably carried out in a fluidized bed coating device known per se to a person skilled in the art.

A subject of the invention is also a method for the conversion of acrolein to acrylic acid, wherein an above-defined catalyst is used.

In the method, acrolein, preferably with oxygen, steam and nitrogen, is passed at 200 to 400° C. over a bed of the catalyst according to aspects of the invention. An improvement with regard to acrolein conversion rate, acrylic acid selectivity and acrylic acid yield is apparent in the method according to aspects of the invention compared with a method which has been carried out with a catalyst according to the state of the art.

The invention is described in more detail with reference to the following embodiment examples and the figures, which are not to be regarded as limitative. The device used corresponds largely to the device described in DE 101 09 892 A1, with the difference that the device used for carrying out the method according to aspects of the invention had no preliminary evaporator stage.

BRIEF DESCRIPTION OF THE FIGURES

There are shown in.

EMBODIMENT EXAMPLES

General

Figure 1:
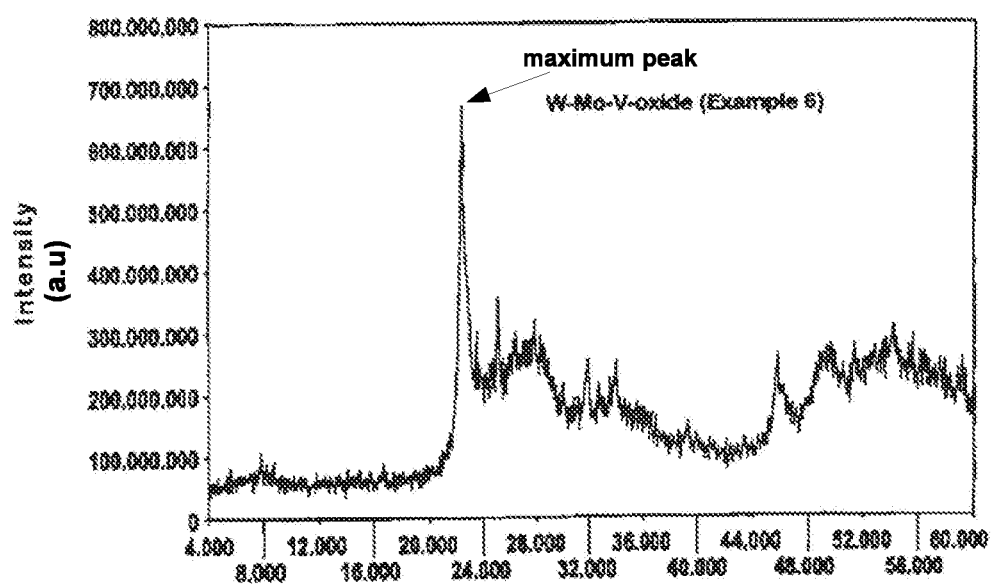
FIG. 1 the XRD spectrum of the molybdenum mixed oxide according to aspects of the invention obtained in Example 6
FIG. 2 the XRD spectrum of the doped mixed oxide according to aspects of the invention obtained in Example 7
Figure 2:
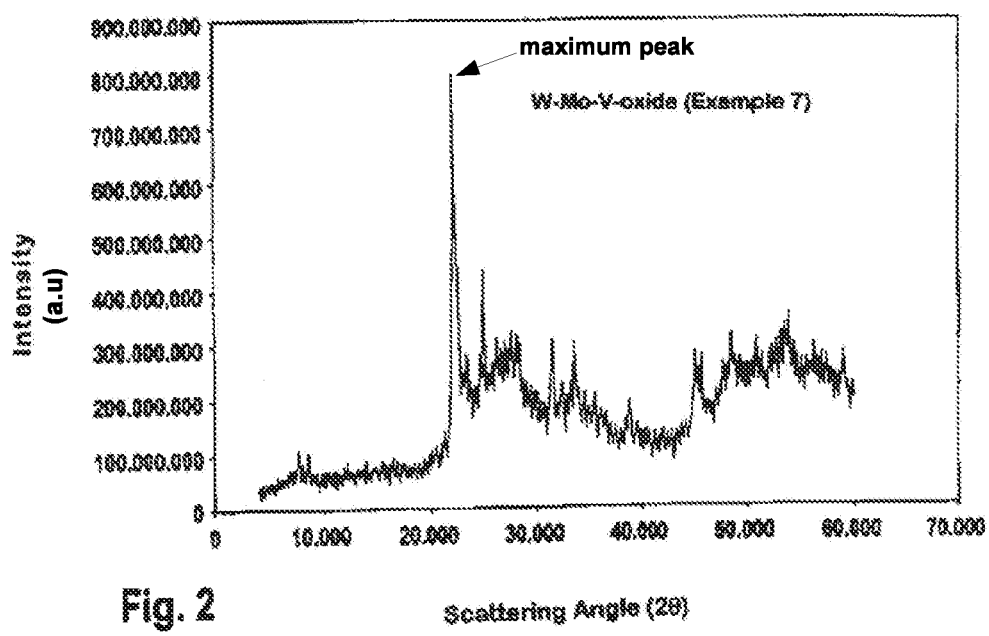

The essential advantages of the preparation with the aid of the pulsation reactor are the reduction of the overall preparation time, the small outlay (only the reactor is needed) and the fact that there is no drying and treatment of the product. The desired BET surface areas, particle sizes and also the crystallinity of the material can be varied in one step by the pulsation reactor.

The following methods were varied for the preparation of the mixed oxides:

Example 1

MoWV Variant 1

Two solutions were produced for the production.
For solution 1, 18 l dist. $H_2O$ was placed in a steel drum and heated. 487.8 g ammonium metatungstate was added and dissolved. Once 70° C. had been reached, 3300 g ammonium heptamolybdate tetrahydrate and 546.6 g ammonium metavandadate were added. Once the components had dissolved completely, 113.4 g antimony trioxide was added and the mixture stirred for 1 hour at 95° C. The solution was cooled to room temperature.

Solution 2 was produced by dissolving 466.8 g copper sulphate in 2880 ml dist. $H_2O$ at room temperature. The two solutions were mixed at room temperature and stirred for approx. 1 h. A suspension formed.

The solution was atomized in the pulsation reactor as follows: after a heating-up period, conditional on the equipment, of several hours, the suspension was sprayed at different reactor temperatures (380, 360, 400° C.).

Air was used as carrier gas. The BET surface areas of the obtained molybdenum mixed oxide were between 1 and 4 $m^2/g$.

Example 2

MoWV Variant 2

For the production, 11820 ml distilled $H_2O$ was introduced. 3150.12 g ammonium heptamolybdate tetraydrate was added to this and dissolved. Continuous stirring was carried out during the whole production process.

822.24 g ammonium metatungstate was then added and dissolved. After subsequent heating to approx. 80° C., 585.6 g ammonium metavanadate was then added and the mixture heated further to 100° C. This temperature was maintained for 5 hours, then the solution was cooled to room temperature.

444 g ammonium acetate was then added, also at room temperature.

Half of the 5 kg batch was doped with iron and copper.

For this, 1.86 g copper acetate and 4.14 g iron nitrate were dissolved in 120 ml dist. $H_2O$ in each case and then added to the solution.

The solution was heated for 12 h under reflux. A clear, orange-red solution formed.

This solution was atomized doped and undoped into the pulsation reactor at 380° C. using air as carrier gas. A grey powder with BET surface areas of 3-4 $m^2/g$ formed.

Example 3

MoWV Variant 3

11820 ml dist. $H_2O$ was placed in a drum. 3150.12 g ammonium heptamolybdate tetrahydrate was added to this, then heated and left until it had completely dissolved.

822.24 g ammonium metatungstate was then added and dissolved. The mixture was then heated to approx. 80° C., then 585.6 g ammonium metavanadate was added and the mixture heated further to 100° C. This temperature was maintained for 5 hours and then cooled to room temperature.

After cooling to room temperature, 444 g ammonium acetate was added. Continuous stirring was carried out during the whole production process.

Doping:

The batch was doped with iron and copper. For this, 3.72 g copper acetate and 8.28 g iron nitrate were dissolved in 240 ml dist. $H_2O$ in each case and then added to the solution.

Atomization+Results:

The solution was atomized in normal air in the pulsation reactor.

Solution with Doping:

| | | | |
|---|---|---|---|
| Temperature: | 380° C. | | |
| Colour of the powder: | grey/black | | |
| BET: | 3.2 | | |
| XRD: | Displays a maximum peak at 22 degrees 2-theta | | |
| Crystallite size: | 210 Å | | |
| Composition: | W 14.7% | Theoretical: | 9.3% |
| | V 6.6% | | 6.2% |
| | Mo 45.9% | | 46.9% |
| | Fe <220 ppm | | 2.5% |
| | Cu 0.15% | | 3.1% |
| Powder from the filter bags | | | |
| Temperature: | 380° C. | | |
| Powder: | grey/black | | |
| BET: | 3.3 | | |
| XRD: | Displays a maximum peak at 22 degrees 2-theta | | |
| Crystallite size: | 201 Å | | |
| Composition: | W 14.6% | | |
| | V 6.7% | | |
| | Mo 46.9% | | |
| | Fe 240 ppm | | |
| | Cu 2.2% | | |

Example 4

MoWV Variant 4

Solution 1: 18 liters dist. $H_2O$ was placed in a steel drum and heated. 487.8 g ammonium metatungstate was added and dissolved. Once the temperature had reached approx. 70° C., 3300 g ammonium heptamolybdate tetraydrate and 546.6 g ammonium metavanadate were added. Once the components had dissolved completely, 113.4 g antimony trioxide was added and the mixture stirred for 1 hour at 95° C. The mixture was then cooled to room temperature. Continuous stirring was carried out during the whole production process.

Solution 2: 466.8 g copper sulphate was dissolved in 2880 ml dist. $H_2O$ at room temperature. After cooling solution 1, the two solutions were mixed and stirred for 1 hour. A black solution with fine white particles formed.

Atomization+Results:

All atomizations were carried out with normal air in the pulsation reactor.

| | | | |
|---|---|---|---|
| Powder from the drum | | | |
| Temperature: | 380° C. | | |
| Powder: | grey/black | | |
| BET: | 1.0 $m^2/g$ | | |
| XRD: | Displays a maximum peak at 22 degrees 2-theta | | |
| Crystallite size: | 207 Å | | |
| Composition | W 9.1% | Theoretical: | 9.3% |
| | V 6.0% | | 6.2% |
| | Mo 45.8% | | 46.9% |
| | Sb 1.8% | | 2.5% |
| | Cu 2.2% | | 3.1% |
| Powder from the filter bags | | | |
| Temperature: | 380° C. | | |
| Powder: | grey/black | | |
| BET: | 1.5 | | |
| XRD: | Displays a maximum peak at 22 degrees 2-theta | | |
| Crystallite size: | 197 Å | | |
| Composition: | W 9.2% | Theoretical: | 9.3% |
| | V 6.1% | | 6.2% |
| | Mo 46.5% | | 46.9% |
| | Sb 1.8% | | 2.5% |
| | Cu 2.2% | | 3.1% |

Example 5

Comparison Example

Example 5 was carried out according to U.S. Pat. No. 6,124,499:

127 g copper(II)acetate monohydrate (Cu content 32.3 wt.-%) was dissolved in 2700 g water (solution I). 860 g ammonium heptamolybdate tetrahydrate (81.3 wt.-% $MoO_3$), 143 g ammonium metavanadate (72.2 wt.-% $V_2O_3$) and 126 g ammonium paratungstate heptahydrate (89.3 wt.-% $WO_3$) were dissolved in succession in 5500 g water at 95° C. (solution II). Solution I was then stirred all at once into solution II and the aqueous mixture spray-dried at an outlet temperature of 110° C. The obtained spray product was kneaded with 0.15 kg water per kg powder.

The kneaded matter was calcined in a convection oven in an oxygen/nitrogen mixture. The oxygen content was set such that the $O_2$ starting concentration was 1.5 vol.-% at the oven outlet. The kneaded material was first heated to 300° C. at a rate of 10° C./min and then kept at 300° C. for 6 h. The mixture was then heated to 400° C. at a heating rate of 10° C./min and kept at 400° C. for 1 h. The catalyst had the composition $Mo_{12}V_3W_{12}Cu_{1.6}O_x$.

The calcined active material was ground down to 0.1 μm to 50 μm.

Powder: grey/black

BET: 1.0 $m^2/g$

XRD: Displays a maximum peak at 22 degrees 2-theta

Crystallite size: >960 Å

Example 6

According to Aspects of the Invention

Solution 1:

18 liters dist. H₂O was placed in a steel drum and heated. 487.8 g ammonium metatungstate was added and dissolved. When the temperature had reached approx. 70° C., 3300 g ammonium heptamolybdate tetrahydrate and 546.6 g ammonium metavanadate were added. Once the components had dissolved completely, 113.4 g antimony trioxide was added and the mixture stirred for 1 h at 95° C. The mixture was then allowed to cool. Continuous stirring was carried out during the whole production process.

Solution 2:

466.8 g copper sulphate was dissolved in 2880 ml dist. H₂O at room temperature.

After cooling solution 1, the two solutions were mixed and stirred for 1 hour. A black solution with fine white particles formed.

After atomization of the solution/suspension at 380° C. in the pulsation reactor, a powder with the following characteristics was obtained:

Powder: grey/black
BET: 5-7 m2/g
XRD: Displays a maximum peak at 22 degrees 2-theta
Crystallite size: 207 Å

Example 7

According to Aspects of the Invention 11820 ml dist. H₂O was placed in a vessel. 3150.12 g ammonium heptamolybdate tetrahydrate was added to this vessel, then the heating was started and continued until everything had completely dissolved.

822.24 g ammonium metatungstate was then added and the mixture was left until everything had dissolved. The mixture was then heated to approx. 80° C., then 585.6 g ammonium metavanadate was added and the mixture heated further to 100° C. This temperature was maintained for 5 hours, followed by cooling to room temperature.

After cooling to room temperature, 444 g ammonium acetate was added. Continuous stirring was carried out during the whole production process.

Doping:

The batch was doped with iron and copper. For this, 3.72 g copper acetate and 8.28 g iron nitrate were dissolved in 240 ml dist. H₂O in each case and then added to the solution.

After atomization of the solution at 380° C. in the pulsation reactor, a powder with the following characteristics was obtained:

Colour of the powder: grey/black
BET: 6
XRD: Displays a maximum peak at 22 degrees 2-theta
Crystallite size: 210 Å

Example 8

Production of Coated Catalysts

A fluidized bed coating device was used to carry out the coating.

The steatite spheres were coated with the various mixed oxide active materials from Examples 5 to 7 under the following conditions:

22.22 g of the powder was weighed into a measuring cylinder, made into a slurry with 500 ml dist. H₂O. The resulting suspension was stirred intensively. 8.89 g binder was then added and the mixture stirred for 1 h on a magnetic stirrer. The "coating" of the produced suspension took place on a weighed-in sample of 80 g steatite spheres of (2-4 mm), wherein the active material charge was 20% (50 g powder per 200 g steatite spheres). The catalyst was then dried in air at 110° C.

Example 9

Determination of the Catalytic Performance Data of the Catalysts 21 g catalyst (i.e. the above-described coated steatite spheres), diluted with 350 g steatite spheres with a diameter of 4.5 mm to avoid hotspots, was poured into a 120-cm long reaction tube with an internal diameter of 24.8 mm to a length of 105 cm. The reaction tube was in a liquid salt bath which was able to be heated to temperatures of up to 500° C. In the catalyst bed there was a 3 mm protective tube with an integrated thermocouple via which the catalyst temperature over the complete catalyst combination was able to be displayed.

To determine the catalytic performance data, acrolein was put into the gas phase by means of a saturator. An air-inert gas mixture was passed through the saturator in such a way and the thermostat temperature of the saturator set such that an acrolein content of 5 vol.-% in the feed gas resulted. The reactor feed consisted of a mixture of 7 vol.-% 0, 10 vol.-% steam and the remainder N₂. The acrolein charge was 150 Nl/1 h at most.

The acrolein conversion rate and the acrylic acid selectivity were determined at an average catalyst temperature of 250° C. The results of the tests with the catalysts which contain the active material according to the examples named in the table are listed in Table 1.

TABLE 1

|  | Example 5 (comparison example, state of the art) | Example 6 (according to the invention) | Example 7 (according to the invention) |
| --- | --- | --- | --- |
| Acrolein conversion rate | 98.3 | 99.2 | 98.7 |
| Acrylic acid selectivity | 95.1 | 95.3 | 95.8 |
| Acrylic acid yield | 93.5 | 94.5 | 94.6 |

The ascertained results demonstrate an improvement of the catalysts according to aspects of the invention with regard to acrolein conversion rate, acrylic acid selectivity and acrylic acid yield compared with a catalyst according to the state of the art.

The invention claimed is:

1. A method for the production of a nanocrystalline molybdenum mixed oxide, comprising the steps of
   a) introducing a solution, suspension or slurry which contains a molybdenum starting compound and ammonium metatungstate into a reaction chamber by means of a carrier fluid,
   b) thermally treating the solution, suspension or slurry which contains the molybdenum starting compound and the ammonium metatungstate in a treatment zone by means of a pulsating flow at a temperature of from 200 to 500° C. to form a nanocrystalline molybdenum mixed oxide, and c) discharging the nanocrystalline molybdenum mixed oxide obtained in step b) from the reactor, wherein a molybdate is used as molybdenum starting compound, and wherein prior to or during the introduction into the reaction chamber, a solution, suspension or slurry of a copper and/or iron salt is added to the solution, suspension or slurry which contains the molybdenum starting compound and the ammonium metatungstate, wherein the nanocrystalline molybdenum mixed oxide obtained in step b) from the reactor is capable of catalysing the conversion of acrolein to acrylic acid.

2. The method according to claim 1, wherein the molybdenum starting compound is ammonium heptamolybdate tetrahydrate.

3. The method according to claim 1, wherein the carrier fluid is a gas.

4. A method for the production of a nanocrystalline molybdenum mixed oxide, comprising the steps of:
   a) introducing a solution, suspension or slurry which contains a molybdenum starting compound and ammonium metatungstate into a reaction chamber by means of a carrier fluid,
   b) thermally treating the solution, suspension or slurry which contains the molybdenum starting compound and the ammonium metatungstate in a treatment zone by means of a pulsating flow at a temperature of from 200 to 400° C. and a pressure of 15 to 40 bar to form a nanocrystalline molybdenum mixed oxide, and
   c) discharging the nanocrystalline molybdenum mixed oxide obtained in step b) from the reactor, wherein a molybdate is used as molybdenum starting compound, and wherein prior to or during the introduction into the reaction chamber, a solution, suspension or slurry of an copper and/or iron salt is added to the solution, suspension or slurry which contains the molybdenum starting compound and the ammonium metatungstate, wherein the nanocrystalline molybdenum mixed oxide obtained in step b) from the reactor is capable of catalysing the conversion of acrolein to acrylic acid.

\* \* \* \* \*